(12) United States Patent
Gorsek

(10) Patent No.: US 6,565,847 B1
(45) Date of Patent: May 20, 2003

(54) THERMOGENIC WEIGHT MANAGEMENT COMPOSITION

(75) Inventor: Wayne F. Gorsek, Boynton Beach, FL (US)

(73) Assignee: Vitacost.com, Inc., Boynton Beach, FL (US)

( * ) Notice: Subject to any disclaimer, the term of this patent is extended or adjusted under 35 U.S.C. 154(b) by 0 days.

(21) Appl. No.: 10/187,617

(22) Filed: Jul. 3, 2002

(51) Int. Cl.⁷ .................. A01N 63/00; A01N 65/00; A61K 38/54
(52) U.S. Cl. .................. 424/93.45; 424/94.2; 424/655; 424/729; 424/736
(58) Field of Search .................. 424/655, 93.45, 424/94.2, 736, 729

(56) References Cited

U.S. PATENT DOCUMENTS 6,383,482 B1 * 5/2002 Gorsek .................. 424/93.45
6,447,818 B1 * 9/2002 Stankov .................. 424/736

* cited by examiner

*Primary Examiner*—Herbert J. Lilling
(74) *Attorney, Agent, or Firm*—Hoffman, Wasson & Gitler, PC

(57) ABSTRACT

A powerful formulation for weight loss containing Green Tea extract, hydroxycitric acid, thermogenic herbs, glucomannan, chromium, and a probiotic. The formulation boasts metabolic rates, suppresses appetite and helps burn fat without having adverse cardiovascular effects.

2 Claims, No Drawings

THERMOGENIC WEIGHT MANAGEMENT COMPOSITION

BACKGROUND OF THE INVENTION

The invention relates to a composition for permanent weight management. The composition burns fat, boosts metabolic rate, controls appetite, eliminates sugar cravings and eating binges. An orally ingested composition is provided which contains effective amounts of vitamins, minerals, herbs and natural extracts with the adverse effects to the cardiovascular system. The composition contains no dangerous stimulants like Ephedrine, commonly known as Ma Huang.

The process by which weight is controlled is so complex that even most talented scientists do not understand it.

Prior formulations such as those disclosed in U.S. Pat. No. 5,626,849 fall short of the unique blend which requires Citrus Aurantium L and Guarana Extract as a key nutrient to provide a feeling of satiation and a calming effect for healthy weight management.

It is an object of the present invention to provide an unique formulation which allows individuals to lose weight and keep it off.

SUMMARY OF THE INVENTION

The key to the unique formulation is a combination of effective amounts of specific vitamins, minerals, herbs and nutrients. These essential components not only burn fat and boost metabolic rate, but they control appetite, eliminate sugar cravings, eating binges and more.

The formulation contains Green Tea Extract, Garcinia Cambogia, Citrus Aurantium L, Guarana Extract, Glucomannan, Chromium such as in the form of chromium picolinate, and a probiotic such as *lactobacillus* (acidophilus).

The formulation is preferably delivered in capsule form at six capsules per day.

DETAILED DESCRIPTION OF THE INVENTION

The present invention involves a composition for oral ingestion that contains an effective amount of standardized Green Tea extract, Guarana, Citrus Aurantium, Glucomannan, Chromium such as in the form of chromium picolinate, a probiotic such as lactobacillus acidophilus and other minor nutrients. More specifically, this formulated produce is a permanent weight management composition. This product allows for excess fat to be burned, metabolic rates to be boosted, appetite to be controlled, eating binges to be curtailed and for the elimination of sugar cravings. The formulation addresses hunger cravings for those with excess energy, hyperactivity or high blood pressure.

In order to secure the desired result the following essential components are provided:

Standardized Green Tea extract (standardized for 20% polyphenols) (leaf), approximately 200 mg, the component inhibits the enzyme that causes the breakdown of norepinephrine, thus causing an increase in metabolic rate. It has also been shown to increase the rate of brown fat metabolism (20mg–2,000 mg).

Garcina Cambogia (standardized for 60% (HCA)) (fruit) (Hydroxy citric acid), reduces appetite and helps prevent excess carbohydrates from being stored as body fat. (Approximately 1500 mg (1.5 g))(150 mg–15,000 mg)

Thermogenic herbs, Guarana (Guarana Est (22% caffeine)) 900 mg and bitter orange (citrus aurantium) 600 mg that promotes weight loss but does not have adverse cardiovascular effects.

Glucomannan is present (150–15,000 mg)

Chromium in the form of chromium picolinate, a mineral, helps insulin to metabolize fat, turns protein into muscle, and converts sugar into energy (400 mcg)(40 mcg–4,000 mcg).

A probiotic such as lactobacillus acidophilus (10–1000 mg) helps balance the digestive system with friendly flora producing many key nutrients like biotin and vitamin K. It also helps inhibit the overgrowth of bad bacteria and yeast. By helping restore peak health to the digestive tract, this probiotic is another key component of the weight management system. The enzymes work with the digestive system to break down food into micronutrients and is more easily assimilated for optimum health and energy.

Also plant source enzymes are present. (50–5000 mg)

In addition to the key components, other components such as kosher gelatin (capsules), magnesium stearate and silicon dioxide are included.

Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

What is claimed is:

1. A weight loss composition comprising an effective amount of:

Green Tea Extract standardized for 20% polyphenols;
Hydroxy Citric Acid;
Citrus Aurantium;
Guarana Extract standardized to 22% polyphenols;
Glucomannan;
Chromium Picolinate; and
*Lactobacillus acidophilus.*

2. A weight loss composition comprising:

200 mg Green Tea Extract;
1500 Mg Hydroxy Citric Acid;
900 Mg Guarana Extract;
600 Mg Citrus Aurantium;
1500 Mg Glucomannan;
400 Mcg Chromium Picolinate; and
100 mg lactobacillus acidophilus.

* * * * *